United States Patent [19]

Gomez et al.

[11] Patent Number: 5,032,657

[45] Date of Patent: Jul. 16, 1991

[54] POLYMERIZABLE 2(2-HYDROXYNAPHTHYL)2H-BENZO-TRIAZOLE COMPOUNDS

[75] Inventors: Peter M. Gomez, Northampton, Mass.; Hermann H. Neidlinger, San Jose, Calif.

[73] Assignee: The United States of America as represented by the United States Department of Energy, Washington, D.C.

[21] Appl. No.: 525,572

[22] Filed: May 21, 1990

[51] Int. Cl.$^5$ .................... C08F 26/06; C07D 249/20; C08J 3/28
[52] U.S. Cl. .................... 526/261; 548/259; 523/114
[58] Field of Search .................... 526/261; 548/259

[56] References Cited

U.S. PATENT DOCUMENTS

| 4,380,643 | 4/1983 | Yoshida et al. | |
|---|---|---|---|
| 4,508,882 | 4/1985 | Yoshida et al. | |
| 4,614,709 | 9/1986 | Sasoki et al. | |
| 4,716,234 | 12/1987 | Dunks et al. | 548/259 |
| 4,719,248 | 1/1988 | Bambury et al. | 523/108 |

OTHER PUBLICATIONS

Carl R. Noller, Chemistry of Organic Compounds, W. B. Saunders Company, 1965, p. 735.

Primary Examiner—Joseph L. Schofer
Assistant Examiner—Wu C. Cheng
Attorney, Agent, or Firm—Kenneth Richardson; James W. Weinberger; William R. Moser

[57] ABSTRACT

Benzotriazole compounds having the formula:

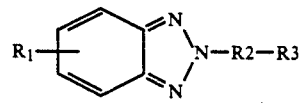

wherein $R_1$ is H, Cl, or $OCH_3$; $R_2$ is a hydroxynaphthyl group; and $R_3$ is a vinyl unsaturated polymerizable group. Homopolymers or copolymers thereof are effective as UV light stabilizers and absorbers.

10 Claims, 4 Drawing Sheets

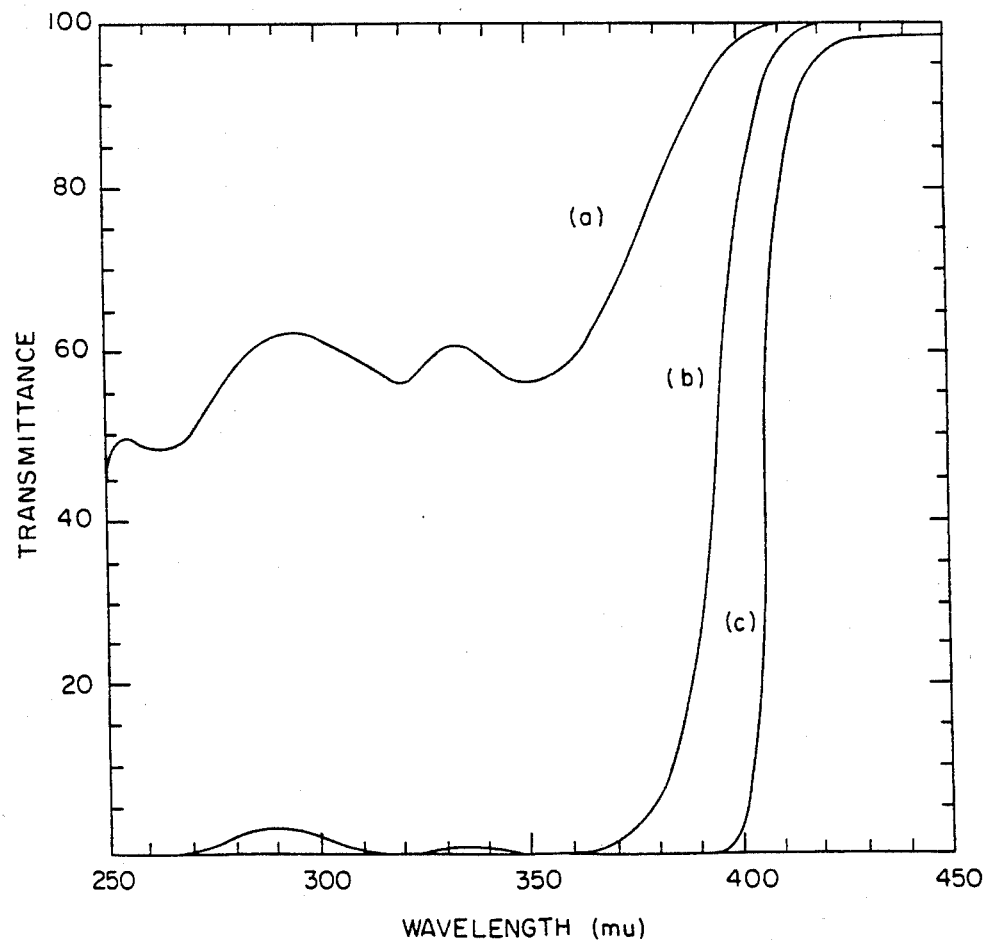

POLYMERIZABLE 2(2-HYDROXYNAPHTHYL)2H-BENZOTRIAZOLE COMPOUNDS

The United States Government has rights in this invention pursuant to Contract No. DE-AC02-83CH10093 between the United States Department of Energy and the Midwest Research Institute.

BACKGROUND OF THE INVENTION

1. Field of Invention The invention relates generally to polymerized benzotriazole compounds as ultraviolet (UV) light stabilizers and absorbers, and the incorporation of these compounds into various plastics. Preferred compounds are 2(2-hydroxynaphthyl) 2H-benzotriazoles. These naphthyl-based benzotriazole compounds are polymerized to provide unique properties that include the combination of high molecular weight and UV absorption at a high transmittance cutoff up to 430 nm.

In this invention, the polymerizable compound group is attached to the naphthyl ring, for which a formula structure is represented as follows:

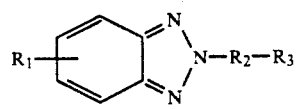

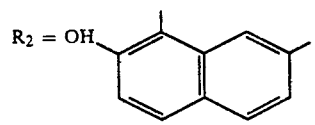

wherein $R_1$ is H, Cl, or $OCH_3$; $R_2$ is a hydroxynaphthyl ring; and $R_3$ is an unsaturated polymerizable group of a wide selection.

2. Description of the Prior Art

It is known that plastics, inclusive of those used for artificial eye lens implants, are harmed by exposure to solar radiation in the wavelengths of about 290-400 nm. Polymer chains or functional groups in the plastics absorb UV radiation from these wavelengths and the instability of the plastics cause deleterious photochemical reactions.

Photochemical reactions may cause the introduction of functional groups into the polymer; degradation of the polymer chain; or the creation of crosslinkage. To prevent these reactions, a UV absorber is incorporated into the polymer plastic to protect it from the potential degradation of solar radiation.

The ideal absorber should be effective for a substantial period of time, it should not cause discoloration or deterioration of the polymer plastic, and it should not leach out when it comes in contact with a solvent or other low-molecular-weight materials. Also, the peak absorption characteristics of the absorber should ideally be in the most sensitive wavelength to which the polymer is exposed.

It is also important to have a high absorbency index (extinction coefficient) in a UV region and nondestructive emission of the absorbed energy. In addition to the desired photochemical properties, a high absorbency index in wavelengths of from about 290-400 nm with an ideal transmittance cutoff to about 400 nm is needed. UV absorbers can be incorporated into eyeglasses, contact lenses, or intraocular lenses to prevent negative effects caused by UV radiation, such as cataract formation, darkening of the eye's lens, photokeratitis, and erythema. UV radiation up to at least 400 nm should be absorbed to provide protection for the cornea, lens and retina.

Various ophthalmic devices have been developed to absorb UV radiation. Although some of these devices to filter out UV radiation, most of these devices stop wavelengths below 360 nm, but allow radiation between the wavelengths of 360 and 430 nm to go through and adversely effect the eye. Furthermore, most of these devices incorporate low-molecular weight compounds that can be leached out of the device through interactions with body fluids and may cause subsequent biotoxicity effects.

U.S. Pat. No. 4,614,709 discloses the use of hydroxyphenyl-based benzotriazole compounds as UV absorbers in silver halide photographic, light-sensitive materials. However, the patent is not directed to or focused on the feasibility of absorption at higher UV ranges and the compounds do not include polymerizable double ring naphthyl derivatives.

U.S. Pat. Nos. 4,380,643 and 4,508,882 disclose the preparation of 2-hydroxyphenyl benzotriazole compounds having a polymerizable unsaturated group on the phenyl ring, which can be homopolymerized or copolymerized with a comonomer to obtain polymeric UV absorbers. These benzotriazole compounds have the formula:

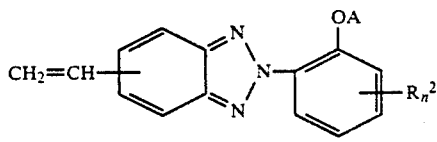

where A represents a hydrogen atom, or an acetyl group; $R^1$ represents a vinyl as shown or haloethyl group or ethyl group; $R^2$ represents a $C_{1-4}$ alkyl group; and n is 1 or 2. $R_2^2$ need not be the same group in a formula.

U.S. Pat. Nos. 4,380,643 and 4,508,882 disclose that the vinylbenzotriazole compounds provide protection in the 300-330 nm UV range of a stated 290-400 nm solar range. Moreover, a reference to the structural formula in these patents shows that the polymerizable functional group is attached to the benzotriazole portion of the compound.

SUMMARY OF THE INVENTION

The object of the invention is to provide benzotriazole compounds as a basis for novel polymeric UV absorbers having higher wavelength cutoffs of up to 430 nm. Particular UV absorbers are 2(2-hydroxynaphthyl) 2H-benzotriazole compounds having polymerizable unsaturated groups attached to the naphthyl double ring.

A further object of the invention is to provide 2(2-hydroxynaphthyl) 2H-benzotriazole compounds having polymerizable unsaturated groups on the naphthyl ring that can be homopolymerized or copolymerized with a comonomer to obtain polymeric UV absorbers having higher wavelength cutoffs of up to about 430 nm.

The benzotriazole compounds of the current invention are characterized by the following structural formula:

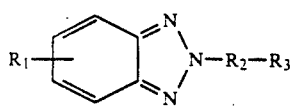

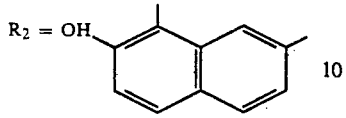

wherein $R_1$ is H, Cl, or $OCH_3$; $R_2$ is a hydroxynaphthyl ring; and $R_3$ is an unsaturated polymerizable group of a wide selection.

In general, the synthetic route for the preparation of polymerizable benzotriazole UV stabilizers uses dihydroxy-substituted naphthalenes.

Starting with 2,7-dihydroxynaphthalene, a coupling reaction with the diazonium salt of nitroaniline was carried out. Reductive cyclization with zinc and sodium hydroxide gave the corresponding benzotriazole stabilizer.

BRIEF DESCRIPTION OF THE DRAWING

FIG. 1 is a UV transmittance spectrum of BDHNM in chloroform at (a) $2\times10^{-5}$ mol/L, (b) $2\times10^{-4}$ mol/L, and (c) $2\times10^{-3}$ mol/L.

FIG. 2 is a UV transmission spectrum of polyhydroxyethyl methacrylate gel (HEMA) without the BDHNM stabilizer.

FIG. 3 is a UV transmission spectrum of 2% by weight BDHNM in HEMA.

FIG. 4 is a UV transmission spectrum of 1% by weight BDHNM in polymethylmethacrylate.

DETAILED DESCRIPTION OF THE INVENTION

The compounds of the invention are prepared by the coupling of 2-nitroaniline diazonium salt with 2,7-dihydroxynaphthalene, and proceeds as follows:

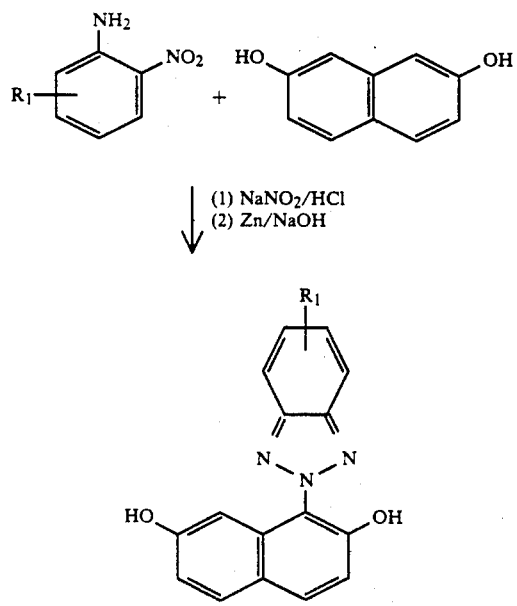

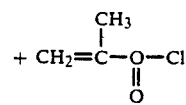

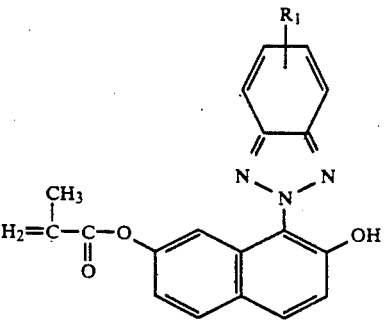

In general, the compounds of the invention are prepared by first performing a standard diazotization, and the 2-nitroaniline diazonium salt is used immediately in a coupling step with 2,7-dihydroxynaphthalene. Next, the azo compound is reductively cyclized with zinc. The material is then acylated with methacryloyl chloride.

The current invention will be further illustrated by the examples, which are provided for purposes of illustration only and are not intended to limit of the current invention.

EXAMPLE 1

2-nitroaniline (0.25 mol, 34.5 g) was warmed with concentrated HCL (95 ml) to form a hydrochloride salt and the solution was cooled to 0° C. and diazotized with a cold solution of sodium nitrite (75.5 g, 0.25 mol) in water (50 ml). The diazonium salt solution added in small portions with vigorous stirring to a solution of 2,7-dihydroxynaphthalene (0.2 mol, 32 g) in ethanol (200 ml) and water (200 ml) at 5° C. and the reaction mixture was stirred for 3 hours at this temperature. The cooling bath was removed and the solution was stirred for 1 additional hour. The red-brown azo dye was then filtered and washed thoroughly with water. The azo dye was suspended in 2N NaOH (300 ml) and the reductive cyclization carried out by the addition of zinc dust (60 g) over a period of 30 minutes followed by the dropwise addition of a NaOH solution (50%). After stirring for 48 hours, the mixture was decanted from the zinc residue and acidified to a pH of 3 to give a crude precipitated product. The product was then carbon decolorized in methanol and recrystallized from a methanol/water mixture to give 30 g (54% yield) of a light brown solid that looked pure by TLC analysis, and was 2(2,7-dihydroxynaphthyl) 2H-benzotriazole (BDHN).

EXAMPLE 2

The procedure of Example 1 was followed using 4-methoxy-2-nitroaniline (0.25 mol, 42 g) in place of 2-nitroaniline to produce 2(2,7-dihydroxynaphthyl)5-methoxy-2H-benzotriazole (MBDHN).

EXAMPLE 3

The procedure of Example 1 was followed using 4-chloro-2-nitroaniline (0.25 mol, 43.3 g) in place of 2-nitroaniline to produce 2(2,7-dihydroxynaphthyl)5-chloro-2H-benzotriazole (CBDHN).

EXAMPLE 4

To a solution of BDHN or 2(2,7-dihydroxynaphthyl) 2H-benzotriazole (5.0 g 18 m mol) and NaOH (0.8 g, 20 m mol) in water (100 ml) a solution of methacryloyl chloride (20 m mol, 4 ml) in chloroform (50 ml) was added dropwise with vigorous stirring. The mixture was stirred for 1 additional hour. The organic layer was separated and washed thoroughly with water before evaporation to yield a crude product that was recrystallized from carbon tetrachloride to give a yellow solid (2.5 g, 40% yield) of 2(2-hydroxy-7-methacryloxynaphthyl) 2H-benzotriazole—m.p. 167°-168° C.

The reaction may be represented as follows:

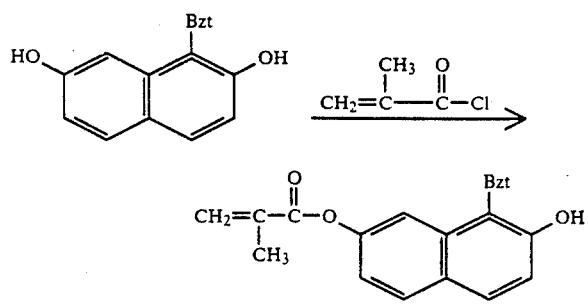

The above reaction of the sodium salt of the free hydroxyl of BDHN with methacryloyl chloride in a water/chloroform Schotten-Baumann reaction gives the polymerizable UV stabilizer BDHNM (55%). After isolating this light yellow solid by precipitation from chloroform and washing it with cold carbon tetrachloride, the UV spectrum of BDHNM in chloroform at $2 \times 10^{-4}$ mol/L showed a $\lambda$ maximum at 352 nm ($\epsilon = 1.3 \times 10^{-4} L/mol\ cm$) with a sharp cut-off at 400 nm in transmission mode at a concentration of $2 \times 10^{-3}$ mol/L see FIG. 1, where (a) is $2 \times 10^{-5}$, (b) is $2 \times 10^{-4}$, and (c) is $2 \times 10^{-3}$ mol/L.

EXAMPLE 5

The procedure of Example 4 was followed using MBDHN (18 m mol, 5.5 g) in place of BDHN to produce a light yellow solid of 2(2-hydroxy-7-methacryloxynaphthyl)5-methoxy-2H-benzotriazole (MBDHNM).

EXAMPLE 6

The procedure of Example 4 was followed using CBDHN (18 mmol, 5.6 g) in place of BDHN to produce a light yellow solid of 2(2-hydroxy-7-methacryloxynaphthyl)5-chloro-2H-benzotriazole (CBDHNM).

EXAMPLE 7

2(2-hydroxy-7-methacryloxynaphthyl) 2H-benzotriazole was copolymerized with methylmethacrylate (MMA) using 2,2'-azobisisobutyronitrile (AIBN) as an initiator as follows:

A 100 mL pear-shaped flask equipped with a magnetic stirrer and side-arm with stopcock was charged with BDHNM (0.1 ) and recrystallized AIBN (50 mg). The flask was capped with a rubber septum and purged with nitrogen. Toluene (10 mL) and dimethyl acetate (5 mL) was added to dissolve the solid completely and methylmethacrylate (10.5 mL, 9.9 g) was added using a syringe. After three freeze-thaw cycles at 0.05 mmHG pressure to degas the homogeneous polymerization mixture, the flask was placed in an oil bath at 60°-65° C. under positive pressure of dry nitrogen. The solution was then stirred for 48 hours at an average temperature of 65° to 68° C. The polymer solution was then dissolved in chloroform (100 mL) and added dropwise to a rapidly stirred beaker of methanol (600 mL) to precipitate a white, fluffy polymer. The sample was then dried overnight in a vacuum oven.

EXAMPLE 8

BDHNM was copolymerized with 2-hydroxyethylmethacrylate (HEMA) and ethyleneglycol dimethacrylate (EGDMA) using 2,2'-azobisisobutyronitrile (AIBN) as an initiator as follows:

A 15 mL polymerization tube was capped with a rubber septum and evacuated. A homogenous mixture of BDHNM (0.1 g), HEMA (9.9 g), EGDMA (0.025 g) and recrystallized AIBN (50 mg), was added to the tube using a syringe. After three freeze-thaw cycles at 0.05 mmHG pressure to degas the polymerization mixture, the tube was placed in a constant temperature bath of 50° C. for 3 days, followed by an oven-curing cycle at 110° C. for 1 day. The product was then cooled to room temperature over a 12-hour period. Soxhlet extraction with water for 5 days failed to extract BDHNM, thus demonstrating the chemically bonded incorporation of the UV-absorbing group in the polymer matrix. A UV transmittance curve for the polymer of this example is plotted in FIG. 3 using a 2 mm thick, unpolished disc cut from the polymer rod produced.

EXAMPLE 9

The procedure of Example 8 was followed using BDHNM (0.1 g), MMA (9.9 g) and AIBN (50 mg). A UV transmittance curve for the polymer of this example in FIG. 4 using a 2 mm thick, unpolished disc cut from the polymer rod produced.

EXAMPLE 10

The procedure of Example 8 was followed using MBDHNM (0.1 g) in place of BDHNM to produce an UV-absorbing xerogel.

While the preferred examples show the preparation of BDHN, BDHNM, and copolymerization of these materials with 2-hyroxyethyl methacrylate and methyl methacrylate, it is to be understood that the type of comonomer is not critical, and it can be any monomer having a polymerizable unsaturated group such as styrene, acrylonitrile, methacrylic esters, acrylic esters, butadiene, isoprene, vinyl chloride, chloroprene, or other vinyl monomers. It is also possible to use polyvinyl compounds such as a divinyl monomer and vinylidene monomers and other compounds having $\alpha,\beta$-unsaturated group. Also, the usual grafting polymerization on the polymer in bulk or solution can provide the polymeric ultraviolet absorbers of the invention.

It is also possible to incorporate these polymerizable UV absorbers in silicone polymers via an addition reaction to —SiH functionalities.

The BDHN and BDHNM monomers can be used as reactive absorbers in a cured polymerizable composition; i.e., as the reactive component for curable polymerizable resin compositions such as unsaturated polyester resin compositions. The curable polymerizable resin composition is then polymerized, then BDHN and BDHNM monomers are also copolymerized with the polymerizable component to obtain a cured product having absorbency.

When the BDHN and BDHNM monomers are used as the copolymerizable component of a polymer, the stability of the polymer to UV rays can be improved with only a relatively low concentration of the BDHN and BDHNM monomers. For example, the copolymer having UV absorbency can be obtained by incorporating only about 0.01 weight percent of the BDHN and BDHNM units or the ratio of the BDHN and BDHNM monomers in the copolymerization can be more than 1 weight percent; however, the maximum ratio is not critical. Nevertheless, when economical factors are considered, the limit of the ratio of the BDHN and BDHNM monomers to the total monomer mixture is about 20 weight percent.

For applications in lens materials, the weight percent of polymerizable stabilizer (BDHNM) may range from as little as 0.1% for screening up to 380 nm and up to 5% for complete absorbance up to 430 nm.

We claim:

1. A homopolymer or copolymer having a vinyl co-monomer of a benzotriazole compound selected from the group of compounds having the formula:

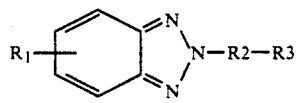

wherein $R_1$ is H, Cl, or $OCH_3$; $R_2$ is a hydroxynaphthyl group; and $R_3$ is a vinyl unsaturated polymerizable group.

2. The copolymer of claim 1, wherein the amount of said vinyl benzotriazole compound in the copolymer is from about 0.01 to about 20 weight percent.

3. The copolymer of claim 2, wherein said unsaturated group is a methacryloxy group.

4. The copolymer of claim 3, further reacted with an ethylenically unsaturated monomer.

5. The composition of claim 4, wherein said ethylenically unsaturated monomer is selected from the group consisting of methyl methacrylate, 2-hydroxyethyl methacrylate, styrene, methylstyrene, vinylsiloxane, acrylamide, acrylonitrile, methacrylonitrile, vinyl acetate, vinyl chloride, vinylidene chloride, vinyl lactam, ethylene, propylene, or mixtures thereof.

6. A benzotriazole compound of the formula:

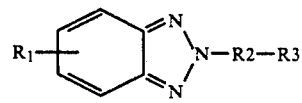

wherein $R_1$ is H, Cl, or $OCH_3$; $R_2$ is a hydroxynaphthyl group; and $R_3$ is a vinyl unsaturated polymerizable group.

7. The compound of claim 6, wherein $R_3$ is a methacryloxy group.

8. The compound of claim 5, wherein said benzotriazole compound is 2-(2-hydroxynaphthyl) 2H-benzotriazole.

9. An optical lens comprising an optically clear polymer of any one of claims 1-5.

10. A plastic film or coating material comprising an optically clear polymer of any one of claims 1-5.

* * * * *